United States Patent [19]

Leskovar et al.

[11] 4,110,686

[45] Aug. 29, 1978

[54] PIEZOELECTRIC-TUNED MICROWAVE CAVITY FOR ABSORPTION SPECTROMETRY

[75] Inventors: Branko Leskovar, Moraga, Calif.; Harold T. Buscher, Orlando, Fla.; William F. Kolbe, Berkeley, Calif.

[73] Assignee: The United States of America as represented by the United States Department of Energy, Washington, D.C.

[21] Appl. No.: 825,503

[22] Filed: Aug. 17, 1977

[51] Int. Cl.² .................................... G01R 27/04
[52] U.S. Cl. .............................. 324/58.5 C; 73/23; 324/71 R
[58] Field of Search ............ 324/58.5 C, 58 C, 71 R; 73/23

[56] References Cited

U.S. PATENT DOCUMENTS 3,889,182 6/1975 Easley et al. ............... 324/58.5 C X

FOREIGN PATENT DOCUMENTS 119,179 11/1970 Denmark ........................... 324/71 R Primary Examiner—Stanley T. Krawczewicz
Attorney, Agent, or Firm—Dean F. Carlson; Roger S. Gaither; Clifton E. Clouse, Jr.

[57] ABSTRACT

Gas samples are analyzed for pollutants in a microwave cavity that is provided with two highly polished walls. One wall of the cavity is mechanically driven with a piezoelectric transducer at a low frequency to tune the cavity over a band of microwave frequencies in synchronism with frequency modulated microwave energy applied to the cavity. Absorption of microwave energy over the tuned frequencies is detected, and energy absorption at a particular microwave frequency is an indication of a particular pollutant in the gas sample.

9 Claims, 2 Drawing Figures

PIEZOELECTRIC-TUNED MICROWAVE CAVITY FOR ABSORPTION SPECTROMETRY

The invention disclosed herein was made under, or in, the course of United States Energy Research and Development Administration Contract No. W-7405-ENG-48 with the University of California.

BACKGROUND OF THE INVENTION

The present invention relates to microwave cavity tuning for gas absorption spectrometry, and more particularly it relates to variable tuning of such a cavity by means of a piezoelectric or a magnetostrictive transducer.

In microwave absorption spectrometry, it is necessary to vary the tuning of a microwave cavity in order to detect an absoprtion peak. Instrumentation known in the art to accomplish this include Stark spectrometer systems with electronic frequency scanning, and a system including a Fabry-Perot confocal resonator using a stepping motor to adjust the resonator spacing to carry out frequency scanning. However, for practical microwave absorption spectrometry of pollutants it is desirable to examine numerous successive samples, with each sample being examined for various pollutants over a range of frequencies, with sensitivity and without changing the chemical or physical properties of the sample being examined. In addition, the instrument used for such spectroscopy should be easily portable from site to site. Although a Stark spectrometer is rapid, it tends to have a low Q and therefore a low sensitivity, it requires a very high operating voltage which may lead to voltage breakdown and disruption of the analysis and destruction of the equipment, it tends to change radicals in a fast radical study due to the required high voltage and it is a large, expensive laboratory instrument with a very sophisticated electronic system and is not easily portable. Another known gas absorption spectrometer system utilizes a Fabry-Perot microwave cavity wherein frequency scanning is accomplished by varying the distance between opposing walls of the microwave cavity by means solely of a servomotor. However, due to the mechanical inertia of the servomotor and the tendency of a servomotor to hunt, such an arrangement is slow; and when many samples are to be sensitively analyzed for a large number of pollutants, such a servomotor system becomes so cumbersome and time consuming as to be impractical.

SUMMARY OF THE INVENTION

In brief, the invention is a microwave cavity that is continuously and rapidly tunable over a wide range of frequencies in synchronism with frequency modulations of microwave energy applied to the cavity, for detecting the presence of a particular gas in a gas sample in the cavity by absorption of microwave energy by the particular gas at its absorption frequency. The cavity includes first and second opposing cavity walls, and a piezoelectric transducer for moving the first wall with respect to the second wall to maintain the cavity in continuous resonance with the applied microwave energy during frequency modulation of the microwave energy.

It is an object of the invention to rapidly and sensitively analyze gas samples for various gaseous pollutants.

Another object is to provide a microwave cavity that is stable and is rapidly continuously adjustable to be in resonance with frequency modulated microwaves applied to the cavity.

Another object is to construct a microwave cavity that is lightweight and compact for incorporation into a portable gas absorption spectrometer.

Other objects and advantageous features of the invention will be apparent in a description of a specific embodiment thereof, given by way of example only, to enable one skilled in the art to readily practice the invention which is described hereinafter with reference to the accompanying drawing.

DESCRIPTION OF AN EMBODIMENT

Figure 1:
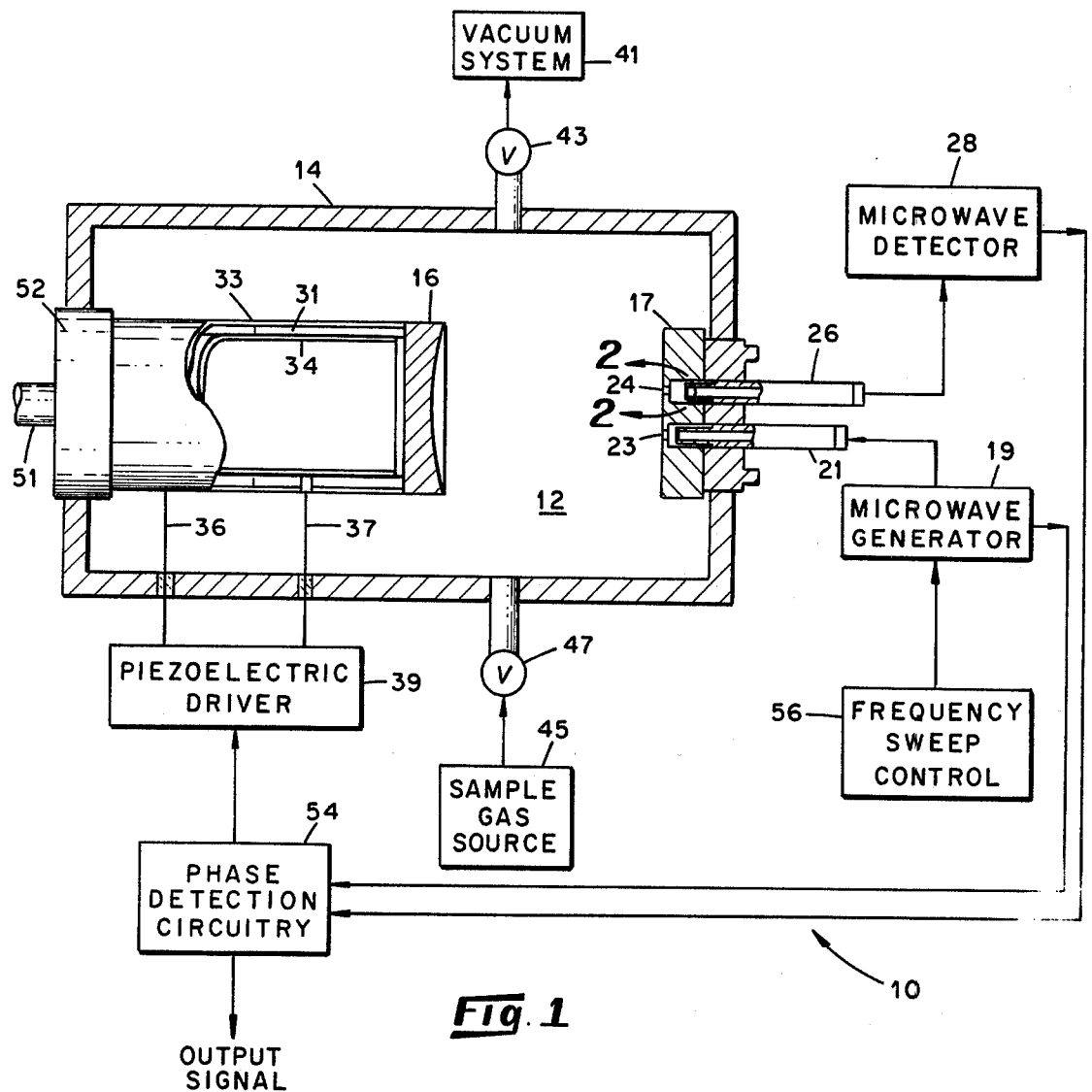
FIG. 1 is a diagram including a cross-sectional view of a microwave cavity provided with two highly polished opposing walls, with one wall moveable by piezoelectric means according to the invention, and further including a block diagram of a gas absorption spectrometer.
Figure 2:
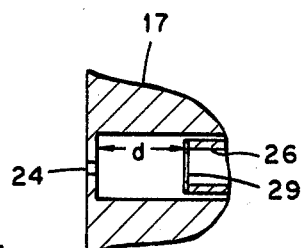
FIG. 2 is an expanded cross-sectional view broken away along lines 2 - 2 of the cavity of FIG. 1 of an iris and output waveguide for coupling energy from the cavity to a detector.

Referring to the drawing, there is shown in FIG. 1 a microwave gas absorption spectrometer 10 including a cavity 12 with an enclosure 14. The active portion of the cavity 12 is defined by first and second opposing cavity walls 16 and 17, both of which may be made flat. However, to maximize the Q of the cavity and to enhance its stability, the wall 16 is made with a concave surface toward the wall 17, and the wall 17 is made flat. To minimize losses the walls are also highly polished. Microwave energy may be coupled to the cavity 12 from a microwave generator 19 over a waveguide 21 which extends through the enclosure 14 and into the wall 17. Two small irises 23 and 24 are provided in the wall 17 to couple energy into and out of the cavity. The iris 23 may be used to couple microwave energy from the waveguide 21 to the cavity 12, and the iris 24 may be used to couple microwave energy from the cavity 12 to a waveguide 26 and a microwave detector 28. The waveguides 21 and 26 may be positioned with respect to the associated iris for optimized minimum transmission loss. The waveguides 21 and 26 are each provided with a mica window to preserve the vacuum integrity of the enclosure 14. In FIG. 2, the waveguide 26 is shown provided with a mica window 29 and spaced an optimized distance d from the iris 24 in the wall 17.

The first wall 16 may be mounted on the end of hollow cylinder 31 of piezoelectric material. The cylinder is provided with an outer electrically conductive coating 33 and an inner electrically conductive coating 34. The coating 34 is spaced from the ends of the cylinder to insure electrical isolation between the coatings. Electrical connections 36 and 37 are provided respectively for the coatings 33 and 34 for application of a voltage across the cylinder from a piezoelectric driver 39.

In operation of the spectrometer 10, the enclosure 14 may be evacuated by means of a vacuum system 41 through a valve 43. The sample of gas to be analyzed may be introduced into the enclosure 14 from a gas sample source 45 through a valve 47. With the gas sample filling the space between the cavity walls 16 and 17, microwave energy is supplied to the cavity 12 from the generator 19. The cavity is tuned to be in resonance with the central frequency of the microwave generator 19 by turning a shaft 51 of a micrometer 52 to which the cylinder 31 is mounted. The spacing between the walls 16 and 17 is thereby adjusted to make the cavity resonant with the applied microwaves. Energy is coupled from the resonant cavity through the iris 24 and waveguide 26 to a microwave detector 28 to develop a corresponding signal that is applied to phase detection circuitry 54. A signal that corresponds to the energy coupled to the cavity 12 from the generator 19 also is applied to the circuitry 54. Comparison of the phase and amplitude of the two signals in the circuitry 54 provides a resultant signal of an amplitude and polarity that may be used to control the piezoelectric driver 39 to apply a voltage between the inner and outer surfaces of the cylinder 31 and thereby move the wall 16 to bring the cavity 12 into precise resonance with the applied microwave energy. The cavity 12 thus is maintained in resonance at all times with the applied microwave energy. However, since the gas sample is to be examined for more than one pollutant, it is necessary to adjust the frequency of the microwave energy applied to the cavity over a range of frequencies that encompass the absorption frequencies of the pollutants for which the gas sample is being examined. Fine tuning to accomplish this may be done by provision of a frequency sweep control 56 for frequency modulating the microwave energy supplied to the cavity 12 from the generator 19. As discussed hereinbefore, any change in the cavity 12 away from resonance is detected and the wall 16 moved accordingly to bring the cavity back into resonance. The gas sample is scanned thereby at a very rapid rate for pollutants. Any pollutants having an absorption frequency within the frequencies scanned absorb microwave energy. This condition may be detected by the detector 28 to supply output signals that may be correlated with the applied frequencies to indicate the amount and kind of pollutants. If it is found necessary to examine samples outside the range of frequencies obtained with the frequency sweep control, rough cavity adjustments may be made by means of a stepping motor coupled to the micrometer shaft 51. Scanning of a gas absorption spectrometer microwave cavity by means of phase detection and frequency sweeping is well known in the art and reference is made to an article by H. E. Radford, "Scanning Microwave Echo Box Spectrometer", The Review of Scientific Instruments, Volume 39, Number 11, November 1968, pages 1687 – 1691, which is incorporated herein by reference and which illustrates the state of the art, but shows a cavity wall moved only by a servomotor to keep the cavity in resonance.

In a specific embodiment of the invention, the cavity 12 was designed to resonate at a central frequency of 70 GHz. The walls 16 and 17 were formed from type 316 stainless steel blanks 1.25 cm thick to have diameters of 5.08 cm, with the wall 16 having a radius of curvature of 14.86 cm. The walls were spaced apart 7.43 cm at their centers, exactly half the radius of curvature. This semiconfocal geometry has the advantage that it is noncritical in alignment, is compact, and exhibits high Q. Resonances occur in this cavity according to the relation $(4s/\lambda) = 2q + \frac{1}{2}$, $(q = 1, 2, 3 \ldots)$ where S is the mirror spacing, $\lambda$ is the wavelength of the radiation in the cavity, and $q$ is the number of standing half waves between the cavity walls. The surfaces of the walls 16 and 17 were highly polished by grinding them true to a few wavelenghts of sodium light, and 75 microns of silver were plated onto each surface which was then coated with 1.5 microns of gold. The irises 23 and 24 were made 0.64 mm in diameter, they were separated 6.2 mm, and the walls of the irises were made 0.13 mm thick. The waveguides 21 and 26 were V-band and fitted into holes behind the irises. The input waveguide 21 was positioned for maximum coupling to the cavity. At a position of $d \cong 4.8$ mm for the output waveguide 26 a minimum transmission loss of 22 db was obtained with a loaded Q of 42,000. The piezoelectric cylinder 31 was 7.62 cm long with an inside diameter of 3.15 cm and an outside diameter of 3.83 cm (two piezoelectric cylinders were used to attain the desired length since none were available from the manufacturer for the full length). A low vapor pressure epoxy was used to secure the wall 16 to the cylinder 31. An electrically conductive coating of silver was applied to both the inner and outer surfaces of the cylinder 31. The cylinder provided about 10 microns of movement of the wall 16 for an applied voltage range of 1500 volts dc. This movement provided for tuning of the cavity 12 over a range of 10 MHz.

The frequency of 70 GHz and the foregoing dimensions of the cavity were selected so that the absorption frequencies of sulfur dioxide and nitrogen dioxide would be maximally detected since these gases are of particular interest in air pollution research. Sulfur dioxide and nitrogen dioxide were detected in gas samples using the specific embodiment with a high sensitivity.

The electrically conductive coatings 33 and 34 and electrical connections 36 and 37 were provided with a protective coating of low vapor pressure epoxy resin at least 1/64 inch thick. The resin was from a TORR-SEAL vacuum sealing kit, Model No. 953-0001, manufactured by Varian Associates, Palo Alto, California. The protective coating protects the connections and conductive coatings from corrosive gases in the samples being analyzed and also inhibits electrical arcing and corona effects.

While an embodiment of the invention has been shown and described, further embodiments or combinations of the invention will be apparent to those skilled in the art without departing from the spirit of the invention.

What we claim is:

1. A tuning device including a microwave cavity for continuously and rapidly tuning the cavity over a wide range of frequencies in synchronism with frequency modulations of microwave energy applied to the cavity, for detecting the presence of a particular gas in a gas sample in the cavity by absorption of microwave energy by the particular gas at its absorption frequency, said tuning device including:

first and second opposing walls defining the cavity; and a piezoelectric transducer for moving said first wall with respect to said second wall to maintain the cavity in continuous resonance with the applied microwave energy during frequency modulation of the microwave energy.

2. The device of claim 1, wherein said piezoelectric transducer includes a hollow cylinder of piezoelectric material and said first wall is secured to one end of the cylinder.

3. The device of claim 2, wherein said cylinder has an inner surface and an outer surface, an electrically conductive coating on said inner surface and another electrically conductive coating on said outer surface, said coatings being electrically separate, said coatings providing conductive surfaces for establishing an electrical field across said inner and outer surfaces to control the elongation of the cylinder and thereby the movement of the first wall and the resonant frequency of the cavity.

4. The device of claim 3, wherein said transducer includes electrical connections to said electrically conductive coatings, and a protective coating over said connections and said conductive coatings.

5. The device of claim 1, wherein said first wall comprises a concave surface facing said second wall, and said second wall comprises a flat surface facing said first wall.

6. The device of claim 4, wherein said concave surface has a radius of curvature that is twice the length of the spacing between said first and second walls at their centers.

7. The device of claim 4, wherein said first and second walls are comprised of a stainless steel substrate, said concave surface and said flat surface of said walls each having a coating of silver over the stainless steel substrate and a coating of gold over the silver coating.

8. The device of claim 1, wherein said second wall includes first and second irises, said first iris for coupling microwave energy into said cavity, and said second iris for coupling microwave energy from said cavity.

9. The device of claim 1, further including a micrometer, said piezoelectric material being mounted on said micrometer to enable spacing said first and second walls apart a precise distance.

* * * * *